United States Patent
Goeser et al.

[11] Patent Number: 6,155,083
[45] Date of Patent: Dec. 5, 2000

[54] ABSORBENT BODY FOR MEDICAL USE

[75] Inventors: Hans Joachim Goeser, Werdau; Egon Gründig, Reichenbach, both of Germany

[73] Assignee: Spinnerei C.B. Goldner GmbH & Co., Werdau, Germany

[21] Appl. No.: 09/021,385

[22] Filed: Feb. 10, 1998

[30] Foreign Application Priority Data

Feb. 14, 1997 [DE] Germany .......................... 197 05 737

[51] Int. Cl.[7] .................................. D04B 23/10
[52] U.S. Cl. ................... 66/170; 66/190; 66/196
[58] Field of Search .................. 66/169 R, 170, 66/190, 191, 197, 193, 194, 196, 202; 28/100, 103, 107, 108; 442/319

[56] References Cited

U.S. PATENT DOCUMENTS

| | | |
|---|---|---|
| 3,395,065 | 7/1968 | Owen, Sr. . |
| 3,695,270 | 10/1972 | Dostal . |
| 3,954,074 | 5/1976 | Wilderman .................. 66/192 |
| 3,967,472 | 7/1976 | Wilderman et al. ............ 66/192 |
| 4,381,805 | 5/1983 | Troy ........................ 139/391 |
| 4,426,414 | 1/1984 | Wilkerson .................. 428/102 |
| 5,192,600 | 3/1993 | Pontrelli et al. ............ 428/102 |
| 5,294,479 | 3/1994 | Longo ...................... 442/313 |
| 5,475,904 | 12/1995 | Le Roy . |

FOREIGN PATENT DOCUMENTS

| | | |
|---|---|---|
| 282587 | 10/1992 | Germany . |
| 4235858 | 3/1994 | Germany . |
| 4330824 | 3/1995 | Germany . |
| 1138040 | 12/1968 | United Kingdom . |
| 2267511 | 12/1993 | United Kingdom . |

*Primary Examiner*—Danny Worrell
*Attorney, Agent, or Firm*—Dennison, Scheiner, Schultz & Wakeman

[57] ABSTRACT

An absorbent body for medical use made of 100% cotton fibers. This absorbent body is distinguished by an upper and a lower cover layer of the cotton fibers made by intermeshing, defining a space therebetween in which the cotton fibers are oriented approximately vertically with respect to the intermeshing.

6 Claims, 1 Drawing Sheet

U.S. Patent  Dec. 5, 2000  6,155,083
Fig. 1
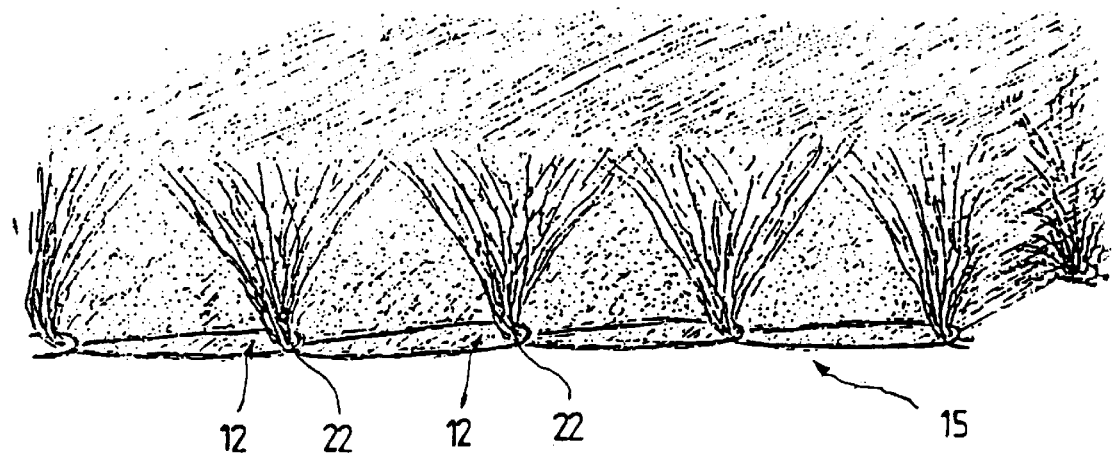
Fig. 2
Fig. 3
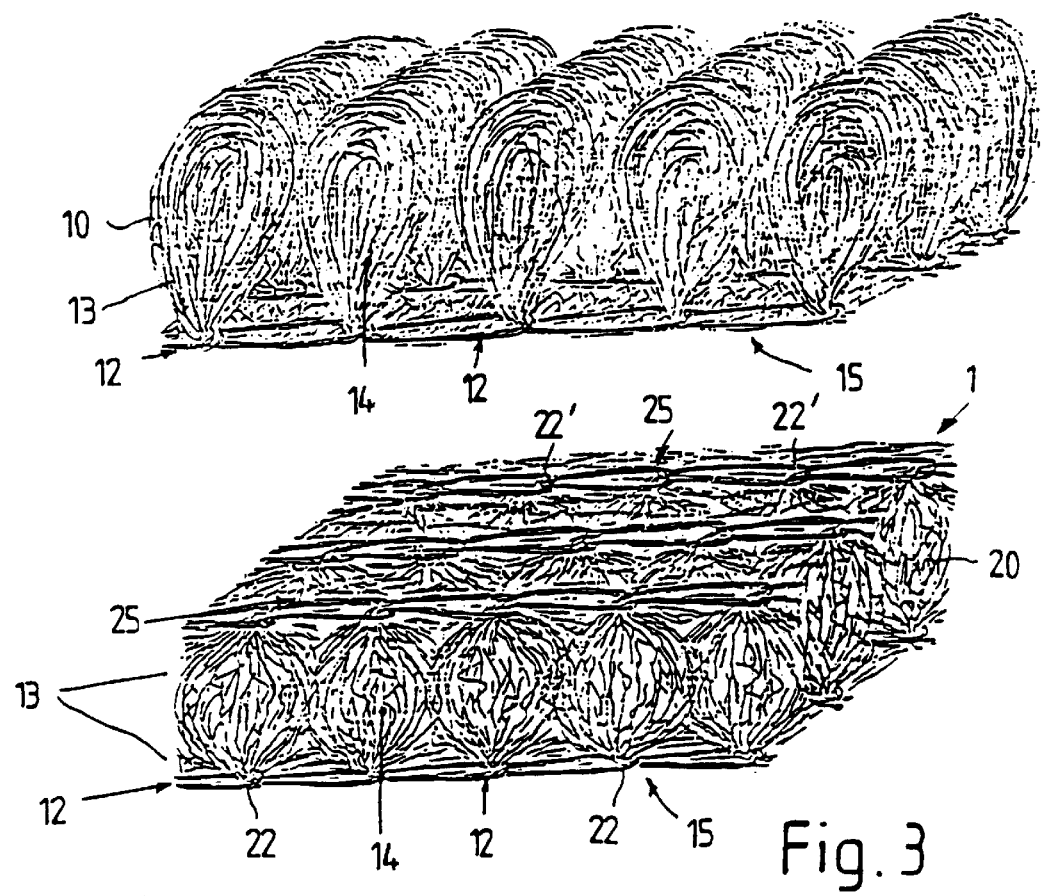

ABSORBENT BODY FOR MEDICAL USE

BACKGROUND OF THE INVENTION

The invention relates to an absorbent body for medical use, made of 100% cotton fibers, and to a method for its production.

Absorbent bodies for medical use are employed for absorbing and removing bodily fluids. They are counted among the so-called staple bandaging materials and must be physiologically safe, dependable and simple to manipulate as well as cost effective.

Initially, loose fibers, preferably natural fibers, are held together in absorbent bodies for medical use either by prior formation of yarn and subsequent weaving, by random positions of the fibers, by quilting or by means of an appropriate cover material, in such a way that the individual fibers are prevented from drifting apart. Only by means of this effect are the absorption of fluids and the storage capability assured, which should amount to a multiple of the inherent weight of the absorbent body. Only if the individual fibers are dependably kept together in the absorbent body is it possible to remove, or respectively draw out the absorbed bodily fluids and take them away.

If the fibers are only insufficiently connected with each other, the absorbent body cannot be removed as a whole, and therefore neither can the fluids it has absorbed. The fibers and fiber remnants which become separated remain in the body and can lead to dangerous defensive reactions.

The ability of an absorbent body to absorb is maximized when all fiber tips are of the same height and are oriented parallel. The storage volume and retaining capacity depend on the so-called capillary effect, i.e. on the distance of parallel oriented fibers from each other, the affinity of the fibers to the secreted matter and the consistency of the secreted matter. The ability of the fibers to bind fluids decreases, the more and the greater the area of the fiber surface is occupied by connecting points with other fibers. Therefore every development of an optimally absorbent body must optimally combine the partially opposing requirements, namely a high degree of fiber integration and a large ability to absorb and retain fluids.

The methods for producing absorbent bodies for medical use, which are part of the prior art and known per se, are the formation of woven or knit materials made of cotton yarn, the production of nonwovens of all types made of cotton, viscose or artificial fibers, as well as quilted or enclosed fibrous webs, or respectively layers of fibers.

Further, an adhesive dressing, for example, is known from the prior art (German Letters Patent 667 940), wherein a support, provided with an adhesive on one side, is used, on which an elastically constituted wound cover made of a woven or knit material is arranged. In this case the support is made of a porous random-fiber nonwoven.

In order to reduce the ability of loose fiber connections to unravel, while maintaining the maximum ability to absorb and retain fluids, it is furthermore a part of the prior art to select combinations between solid and loose connections, for example cotton wool with nonwoven materials or woven envelopes, or absorption layers with woven or non-woven covers. The disadvantage of these bonded layers lies in their insufficient interlocking with each other, or respectively the relatively elaborate production and, in case of a chemical connection between the layers themselves, their lack of physiological safety.

SUMMARY OF THE INVENTION

It is accordingly the object of the instant invention to provide an absorbent body for medical use as well as a method for its production, where the finished product has great fluid absorption and retention ability, together with strong fiber bonding.

In accordance with the invention, this object is attained in connection with an absorbent body for medical use made of 100% cotton fibers by means of a top and bottom cover layer of the cotton fibers made by intermeshing, the fibers being oriented approximately vertically with respect to the intermeshing while forming a space in between. The intermeshing and the cotton fibers can be combined in accordance with the required firmness. Further, the cotton fibers can be oriented closely and approximately parallel in accordance with their consistency and amounts.

In a further embodiment of the invention there is the option of at least one intermeshed cover layer having an insert which, for example, can be woven gauze.

The method for producing an absorbent body for medical use made of 100% cotton fibers provides that the cotton fibers are directly intermeshed on one side for forming a lower cover layer, that subsequently the initially still open top of the cotton fibers is intermeshed to form an upper cover layer, and that a space remains between the loop layers of the top and lower cover layers, in which the cotton fibers are oriented to a large extent vertically to the intermeshing.

Thus, in accordance with the invention an intermeshed fiber structure is advantageously created as a cost-efficient fiber bonding, wherein the ratio of solidity of the fiber bonding and the fluid absorption are optimally combined. In the process, the 100% cotton fibers are rigidly intermeshed with a fluid-permeable or -impermeable cover layer. Only the fiber ends are solidly bonded. These are either wales or transverse connections between the wales. The main portion of the cotton fibers remains arranged vertically and parallel in respect to each other and is therefore fully available to perform its function of retaining fluids.

Advantageously, the fiber bonding can no longer be dissolved into its components when used. The fiber bonds are caused mechanically, i.e. without chemical additives, and thus in a physiologically safe way. As explained above, the cotton fibers lie closely and relatively parallel next to each other. The ability to absorb fluids and the ability to retain fluids in relation to the built-in fiber weight is advantageously maximized by this fiber structure, i.e. the novel absorbent body for medical use.

The invention will be described in more detail in what follows by means of an exemplary embodiment represented in the drawings.

BRIEF DESCRIPTION OF THE DRAWINGS

FIGS. 1 to 3 represent different process steps in a schematic view for producing an absorbent body for medical use in accordance with the invention.

DESCRIPTION OF THE PREFERRED EMBODIMENTS

In accordance with FIG. 1, bundled, 100% cotton fibers 10 are provided, which are provided with an intermeshing 12 for forming a lower cover layer 15. Thus there are loops 22. However, in this case the cotton fibers 10 are bonded only to the extent that, in accordance with FIG. 2, a large portion still remains free for their actual function as the absorption area 13, in which fluid is retained.

Subsequently, the top of the cotton fibers 10, which initially is still open, is intermeshed to form an upper cover layer 25 in accordance with FIG. 3. Thus there are loops 22'.

As can be seen, a space 20 remains between the upper cover layer 25 and the lower cover layer 15, in which the cotton fibers 10 are aligned to a large extent in a vertical direction 14 with respect to the intermeshing 12. This orientation is superior to the random layers of a nonwoven or of a fibrous web of cotton wool, because the ability to store and retain fluids in the absorption area 13 is considerably higher in relation to the amount of cotton fibers used. On the other hand, because of the intermeshed cover layers 15 and 25, there is solid fiber bonding.

For absorbing fluids, the cotton fibers 10 are aligned optimally densely and parallel, depending on their consistency and amount. The loops 22 and the cotton fibers 10 are optimally combined as a function of the required sturdiness of the absorption body 1.

Methods, known per se, can be employed for producing an absorbent body for medical use in accordance with the instant invention, such as, for example, a method for producing a large- volume nonwoven material with surfaces compacted on one side (DE 43 09 990 A1). However, up to now this known method has only been used for producing a nonwoven material for sound abatement, heat insulating materials, filtering purposes and for upholstery combinations. In accordance with a further known technology (DE 42 18 234 C2), a nonwoven material is produced which up to now had been used for floor coverings, ceilings and as insulating materials.

Further, Malimo methods are the knit and the multiknit methods which up to now, however, have not yet been used for producing a material for absorbent bodies for medical use.

Altogether an absorbent body for medical use has been created, which has a high degree of fiber bonding along with a large fluid absorption and retention ability.

What is claimed is:

1. A method for producing an absorbent body for medical use from a body of 100% cotton fibers having an upper surface and a lower surface, comprising the steps of:

directly intermeshing the cotton fibers on the lower surface thereof for forming a bottom cover layer with loops therein;

subsequently intermeshing the cotton fibers on the upper surface thereof to form a top cover layer with loops therein; and defining between the loops of the top and bottom cover layers, a space in which the cotton fibers are oriented substantially perpendicularly with respect to the top cover layer and the bottom cover layer.

2. The method in accordance with claim 1, wherein the cotton fibers are aligned densely and approximately parallel between the upper and lower cover layers in accordance with their consistency and amount.

3. An absorbent body for medical use comprising a body of 100% cotton fibers having an upper surface and a lower surface, a top cover layer formed on said upper surface from said cotton fibers by intermeshing and a bottom cover layer formed on said lower surface from said cotton fibers by intermeshing, the top cover layer and the bottom cover layer defining therebetween a space in which the cotton fibers are aligned generally perpendicularly to the top cover layer and the bottom cover layer.

4. The absorbent body in accordance with claim 1, wherein the cotton fibers are aligned densely and approximately parallel in accordance with their consistency and amount.

5. The absorbent body in accordance with claim 3, wherein at least one of said top cover layer and said bottom cover layer comprises an insert.

6. The absorbent body in accordance with claim 5, wherein the insert comprises woven gauze.

* * * * *